(12) United States Patent
Bolinger et al.

(10) Patent No.: US 8,587,319 B1
(45) Date of Patent: Nov. 19, 2013

(54) BATTERY OPERATED FLAME IONIZATION DETECTOR

(75) Inventors: Jeremy Bolinger, League City, TX (US); Kevin Moses, League City, TX (US)

(73) Assignee: LDARtools, Inc., League City, TX (US)

( * ) Notice: Subject to any disclaimer, the term of this patent is extended or adjusted under 35 U.S.C. 154(b) by 303 days.

(21) Appl. No.: 12/901,346

(22) Filed: Oct. 8, 2010

(51) Int. Cl.
*G01L 21/32* (2006.01)

(52) U.S. Cl.
USPC .......................... 324/462; 324/460; 324/464

(58) Field of Classification Search
USPC ............ 324/462, 464, 460; 55/158; 73/23.22, 73/27 R, 40.7; 356/437; 422/54, 83; 431/25, 69, 78; 701/207; 702/85; 707/102
See application file for complete search history.

(56) References Cited

U.S. PATENT DOCUMENTS

| | | | |
|---|---|---|---|
| 3,853,455 A | 12/1974 | Riordan et al. | |
| 3,976,450 A * | 8/1976 | Marcote et al. | 96/12 |
| 3,985,509 A | 10/1976 | Trone et al. | |
| 4,182,740 A | 1/1980 | Hartmann et al. | |
| 4,316,381 A * | 2/1982 | Woodruff | 73/31.05 |
| 4,346,055 A | 8/1982 | Murphy et al. | |
| 4,603,235 A | 7/1986 | Crabbe, Jr. | |
| H572 H | 2/1989 | Hansen | |
| 5,099,437 A | 3/1992 | Weber | |
| 5,206,818 A | 4/1993 | Speranza | |
| 5,356,594 A | 10/1994 | Neel et al. | |
| 5,432,095 A | 7/1995 | Forsberg | |
| 5,479,359 A | 12/1995 | Rogero et al. | |
| 5,485,620 A * | 1/1996 | Sadre et al. | 717/162 |
| 5,563,335 A | 10/1996 | Howard | |
| 5,655,900 A * | 8/1997 | Cacciatore | 431/70 |
| 5,752,007 A * | 5/1998 | Morrison | 703/2 |
| 5,899,683 A * | 5/1999 | Nolte et al. | 431/25 |
| 6,042,634 A * | 3/2000 | Van Tassel et al. | 95/14 |
| 6,252,510 B1 | 6/2001 | Dungan | |
| 6,341,287 B1 | 1/2002 | Sziklai et al. | |
| 6,345,234 B1 | 2/2002 | Dilger et al. | |
| 6,438,535 B1 | 8/2002 | Benjamin et al. | |
| 6,478,849 B1 | 11/2002 | Taylor et al. | |
| 6,497,136 B2 * | 12/2002 | Satou | 73/23.22 |
| 6,545,278 B1 | 4/2003 | Mottier et al. | |

(Continued)

FOREIGN PATENT DOCUMENTS

| | | | |
|---|---|---|---|
| EP | 0378674 B1 * | 9/1996 | |
| EP | 1329725 A2 * | 7/2003 | |
| WO | 2006-022648 A1 | 3/2006 | |

OTHER PUBLICATIONS

USPTO Allowance (Jun. 8, 2011); U.S. Appl. No. 11/668,367 (Skiba, et al).

(Continued)

*Primary Examiner* — Arleen M Vazquez
*Assistant Examiner* — Giovanni Astacio-Oquendo
(74) *Attorney, Agent, or Firm* — Pramudji Law Group PLLC; Ari Pramudji

(57) ABSTRACT

A method for maintaining one or more operating conditions within a battery operated flame ionization detector (BOFID). The method includes receiving one or more desired values that correspond to the operating conditions and receiving one or more measured values from one or more sensors configured to monitor the operating conditions. After receiving the desired values and the measured values, the method sends one or more commands to a controller disposed inside the BOFID to achieve the desired values based on the measured values.

54 Claims, 7 Drawing Sheets

(56) References Cited

U.S. PATENT DOCUMENTS

| | | |
|---|---|---|
| 6,549,916 B1 | 4/2003 | Sedlar |
| 6,609,090 B1 | 8/2003 | Hickman et al. |
| 6,672,129 B1 | 1/2004 | Frederickson et al. |
| 6,680,778 B2 | 1/2004 | Hinnrichs et al. |
| 6,722,185 B2 | 4/2004 | Lawson et al. |
| 6,771,744 B1 | 8/2004 | Smith et al. |
| 7,017,386 B2 | 3/2006 | Liu et al. |
| 7,089,530 B1 | 8/2006 | Dardinski et al. |
| 7,103,610 B2 | 9/2006 | Johnson et al. |
| 7,136,904 B2 | 11/2006 | Bartek et al. |
| 7,298,279 B1 | 11/2007 | Badon et al. |
| 7,330,768 B2 | 2/2008 | Scott et al. |
| 7,356,703 B2 | 4/2008 | Chebolu et al. |
| 7,369,945 B2 | 5/2008 | Miller et al. |
| 7,437,362 B1 | 10/2008 | Ben-Natan |
| 7,568,909 B2 * | 8/2009 | MacNutt et al. ............ 431/69 |
| 7,588,726 B1 | 9/2009 | Mouradian et al. |
| 7,657,384 B1 | 2/2010 | Moses |
| 7,840,366 B1 | 11/2010 | Moses et al. |
| 7,851,758 B1 | 12/2010 | Scanlon et al. |
| 7,908,118 B2 | 3/2011 | Trowbridge et al. |
| 8,034,290 B1 | 10/2011 | Skiba et al. |
| 2002/0026339 A1 | 2/2002 | Frankland et al. |
| 2002/0080032 A1 | 6/2002 | Smith et al. |
| 2002/0092974 A1 | 7/2002 | Kouznetsov |
| 2002/0094498 A1 | 7/2002 | Rodriguez-Rodriguez et al. |
| 2002/0178789 A1 | 12/2002 | Sunshine et al. |
| 2003/0012696 A1 | 1/2003 | Millancourt |
| 2003/0081214 A1 | 5/2003 | Mestha et al. |
| 2003/0085714 A1 | 5/2003 | Keyes et al. |
| 2003/0217101 A1 | 11/2003 | Sinn |
| 2004/0005715 A1 | 1/2004 | Schabron et al. |
| 2004/0011421 A1 | 1/2004 | Bartlett et al. |
| 2004/0059539 A1 | 3/2004 | Otsuki et al. |
| 2004/0204915 A1 | 10/2004 | Steinthal et al. |
| 2004/0226345 A1 | 11/2004 | McCoy et al. |
| 2004/0258213 A1 | 12/2004 | Beamon et al. |
| 2005/0000981 A1 | 1/2005 | Peng et al. |
| 2005/0005167 A1 | 1/2005 | Kelly et al. |
| 2005/0053104 A1 | 3/2005 | Kulp et al. |
| 2005/0060392 A1 | 3/2005 | Goring et al. |
| 2005/0117641 A1 | 6/2005 | Xu et al. |
| 2005/0234934 A1 | 10/2005 | Mackay et al. |
| 2005/0246112 A1 | 11/2005 | Abhulimen et al. |
| 2005/0262995 A1 | 12/2005 | Kilkis |
| 2005/0267642 A1 | 12/2005 | Whiffen et al. |
| 2005/0275556 A1 | 12/2005 | Brown |
| 2005/0286927 A1 | 12/2005 | Brenner |
| 2006/0020186 A1 | 1/2006 | Brister et al. |
| 2006/0220888 A1 | 10/2006 | Germouni et al. |
| 2006/0235611 A1 | 10/2006 | Deaton et al. |
| 2006/0246592 A1 | 11/2006 | Hashmonay |
| 2006/0286495 A1 | 12/2006 | Roussel |
| 2006/0286945 A1 | 12/2006 | Reznik et al. |
| 2007/0000310 A1 | 1/2007 | Yamartino et al. |
| 2007/0004381 A1 | 1/2007 | Larson et al. |
| 2007/0139183 A1 | 6/2007 | Kates |
| 2007/0299953 A1 | 12/2007 | Walker et al. |
| 2008/0021717 A1 | 1/2008 | Kaartinen et al. |
| 2008/0063298 A1 | 3/2008 | Zhou et al. |
| 2008/0092625 A1 | 4/2008 | Hinnrichs |
| 2008/0120043 A1 | 5/2008 | Miller et al. |
| 2008/0229805 A1 * | 9/2008 | Barket et al. ............ 73/31.01 |
| 2008/0231719 A1 | 9/2008 | Benson et al. |
| 2009/0315669 A1 | 12/2009 | Lang et al. |
| 2010/0211333 A1 | 8/2010 | Pruet et al. |

OTHER PUBLICATIONS

RCE Amendment (Jun. 22, 2011) and USPTO Advisory Action (Jun. 7, 2011); U.S. Appl. No. 12/133,920 (Moses, et al).

Response to Office Action (Aug. 29, 2011), USPTO Office Action (May 27, 2011); U.S. Appl. No. 12/474,504 (Bolinger, et al).

Response/Amendment After Final (Aug. 24, 2010); Final Office Action (Jun. 25, 2010); Response to Office Action (Apr. 26, 2010); and Office Action (Jan. 25, 2010); U.S. Appl. No. 11/686,367 (Skiba, et al).

Response to Office Action (Jul. 13, 2010); Office Action (Apr. 14, 2010); Response/Amendment After Final (Mar. 29, 2010); Final Office Action (Jan. 29, 2010); Response to Office Action (Nov. 4, 2009); and Office Action (Aug. 4, 2010); U.S. Appl. No. 12/032,499 (Moses, et al).

Office Action (Sep. 27, 2010); U.S. Appl. No. 12/133,920 (Moses, et al).

*Environmental Analytics, Inc.* v. *TMX2, Inc. and LDAR Solutions, Ltd.*; Case 4:08-cv-03353; USDC, Southern District of Texas; First Amended Complaint; Dec. 10, 2008.

"2nd Annual Fugitive Emissions—Leak Detection and Repair Symposium"; ISA Technical Conference Brochure; Nov. 2002.

"Introducing the Allegro CX(TM) Field Computer"; Product Newswire (product announcement); Jun. 21, 2004.

"New from Accutech, Wireless Acoustic Monitor Field Units Make Fugitive Emissions Monitoring Compliance Easy"; Product Announcement/Description; Feb. 10, 2004.

"LDARManager™ Makes Fugitive Emission Monitoring a Breeze TISCOR launches its newest product for Leak Detection and Repair"; product announcement/description; Nov. 8, 2002.

Response to Office Action (Feb. 21, 2012) and USPTO Office Action (Nov. 18, 2011); U.S. Appl. No. 12/359,196 (Moses, et al.).

Response to Office Action (Mar. 21, 2011), Office Action (Dec. 21, 2010), RCE (Sep. 27, 2010), Advisory Action (Sep. 10, 2010); U.S. Appl. No. 11/668,367 (Skiba, et al).

Response After Final (May 23, 2011), Final Office Action (Mar. 22, 2011), Response to Office Action (Dec. 27, 2010); U.S. Appl. No. 12/133,920 (Moses, et al).

"Bluetooth Tutorial—Specifications"; Palo Wireless: Bluetooth Resource Center [online]; Jan. 5, 2006; retrieved Dec. 23, 2009 via Internet Archive Wayback Machine.

USPTO Final Action (Jul. 12, 2012) and Response to Office Action (Apr. 24, 2012); U.S. Appl. No. 12/814,265 (Moses).

USPTO Office Action (Jan. 24, 2012)—U.S. Appl. No. 12/814,265 (Moses).

Office Action (Aug. 4, 2009); U.S. Appl. No. 12/032,499 (Moses et al).

Response to Office Action (Feb. 22, 2012 ) and USPTO Office Action (Nov. 22, 2011); U.S. Appl. No. 12/463,770 (Moses).

USPTO Notice of Allowance (May 3, 2012); U.S. Appl. No. 12/474,504 (Bolinger et al.).

Sylvers, Eric ; Wireless: The story of 'Wi'-Technology—International Herald Tribune; Apr. 2006; http://www.nytimes.com/2006/04/17/technology/17iht-wireless18.1550306.html?pagewanted=print (retrieved May 17, 2011).

USPTO Office Action (Nov. 22, 2011); U.S. Appl. No. 12/463,770 (Moses).

RCE Amendment (Jun. 22, 2011) and USPTO Advisory Action (Jun. 7, 2011); U.S. Appl. No. 12/133,920 (Moses et al).

USPTO Office Action (Mar. 6, 2013)—U.S. Appl. No. 12/463,770 (Moses).

\* cited by examiner

BATTERY OPERATED FLAME IONIZATION DETECTOR

BACKGROUND

1. Field of the Invention

Implementations of various technologies described herein are directed to flame ionization detectors (FIDs) and to various methods and/or systems for monitoring and controlling various operating conditions inside the FIDs.

2. Description of the Related Art

The following descriptions and examples do not constitute an admission as prior art by virtue of their inclusion within this section.

Industrial plants that handle volatile organic compounds (VOCs) sometimes experience unwanted emissions of those compounds into the atmosphere from point sources, such as smokestacks, and non-point sources, such as valves, pumps, and/or vessels containing the VOCs. Emissions from non-point sources typically occur due to leakage of the VOCs from joints and/or seals and may be referred to herein as "fugitive emissions". Fugitive emissions from control valves typically occur as leakage through the packing set around the valve stem. Control valves used in demanding service conditions involving large temperature fluctuations and frequent movements of the valve stem commonly suffer accelerated deterioration of the valve stem packing set.

The United States Environmental Protection Agency (EPA) has promulgated regulations specifying a maximum permitted leakage of certain hazardous air pollutants, such as benzene, toluene, 1,1,1-trichloroethane, from certain hardware or fixtures, e.g., control valves. Fugitive emissions are typically monitored using a VOC detector, like a FID, which may also be referred to as a vapor analyzer. In order to more accurately test for leakage of VOCs, various operating conditions inside the FID should remain constant.

SUMMARY

Described herein are implementations of various techniques for maintaining the operating conditions of a battery operated flame ionization detector (FID). In one implementation, a method for maintaining the operating conditions may include receiving one or more desired values that correspond to the operating conditions and receiving one or more measured values from one or more sensors configured to monitor the operating conditions. After receiving the desired values and the measured values, the method may send one or more commands to a controller disposed inside the BOFID to achieve the desired values based on the measured values.

In another implementation, the method for maintaining the operating conditions may include receiving one or more desired values that correspond to the operating conditions and receiving one or more temperature values measured by a temperature sensor disposed inside the BOFID but outside a detector region of the BOFID. After receiving the desired values and the temperature values, the method may determine one or more compensation commands to compensate for one or more effects on one or more tubes inside the BOFID based on the temperature values. The method may then send the compensation commands to a controller disposed inside the BOFID to achieve the desired values based on the temperature values.

In yet another implementation, the method for maintaining the operating conditions may include receiving one or more air pressure values measured by one or more sensors disposed between a probe and a detector region of the BOFID and receiving one or more time stamps that correspond to the air pressure values. After receiving the air pressure values and the time stamps, the method may determine a downstream pressure rate-of-change value based on a change in the air pressure values and the time stamps. Using the rate-of-change, the method may send one or more commands to a controller disposed in the BOFID to turn off an air pump.

In still another implementation, the method for maintaining the operating conditions may include receiving one or more current consumption values of an air pump disposed between a probe and a detector region of the BOFID and receiving one or more time stamps that correspond to the current consumption values. After receiving the current consumption values and the time stamps, the method may determine a current consumption rate-of-change value based on a change in the current consumption values and the time stamps. The method may then send one or more commands to a controller disposed in the BOFID to turn off the air pump based on the current consumption rate-of-change value.

In still yet another implementation, the method for maintaining the operating conditions may include receiving a power shut off value for an air pump disposed in the BOFID. The method may then determine a percentage of power being used by the air pump, and send one or more commands to a controller disposed in the BOFID to turn off a voltage supply coupled to the air pump when the percentage of power is equal to or greater than the power shut off value.

In yet another implementation, the method for maintaining the operating conditions may include receiving one or more measured values from one or more sensors disposed between a filter system and a detector region inside the BOFID. The method may then compare the measured values to a predetermined value. Based on the comparison, the method may display a message indicating that a filter in the filter system should be replaced.

Described herein are implementations of various technologies for a battery operated flame ionization detector (BOFID). In one implementation, the BOFID may include a detector region that has a temperature sensor for measuring the temperature inside the detector region and a humidity sensor for measuring the humidity inside the detector region. The BOFID may also include an air pump for pumping one or more air samples from outside the BOFID to the detector region, a downstream air pressure sensor for measuring air pressure between the air pump and the detector region, a voltage regulator for supplying a voltage to the air pump, and a controller coupled to the temperature sensor, the humidity sensor, the downstream air pressure sensor and the voltage regulator.

In another implementation, the BOFID may include a detector region for determining a presence of a volatile organic compound (VOC) using a flame, a temperature sensor for measuring the temperature outside the detector region, an air pump for pumping one or more air samples from outside the BOFID to the detector region and a downstream air pressure sensor for measuring air pressure between the air pump and the detector region. The BOFID may also include a voltage regulator for supplying a voltage to the air pump and a controller coupled to the temperature sensor, the downstream air pressure sensor and the voltage regulator.

In yet another implementation, in addition to the items listed above, the BOFID may include a Global Positioning System (GPS) device, a hydrogen storage tank coupled to the detector region and a filter system configured to prevent debris from entering the detector region.

In still another implementation, in addition to the items listed above, the BOFID may include a filter sensor between the filter system and the detector region.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein.

DETAILED DESCRIPTION

Figure 1:
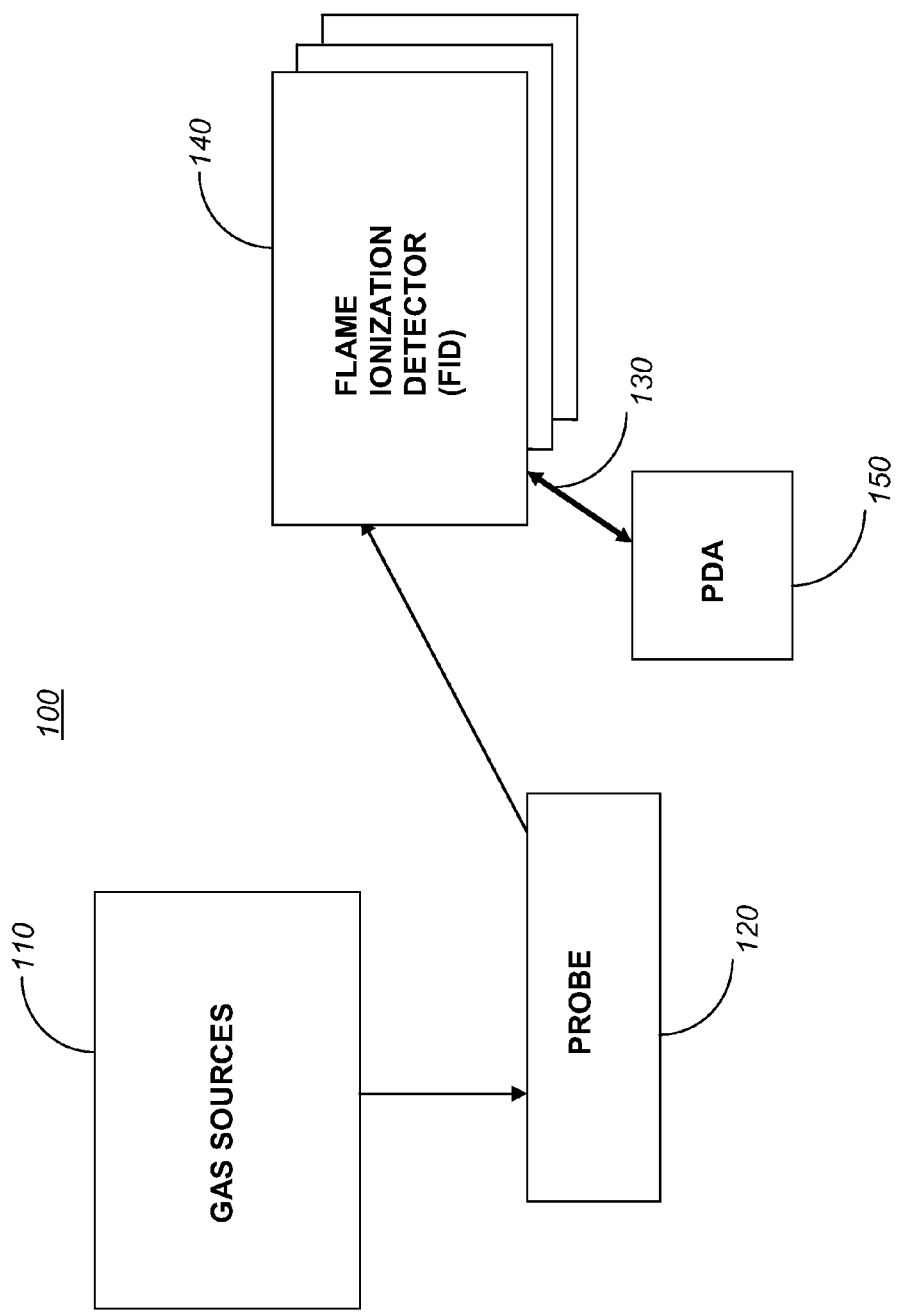
FIG. 1 illustrates a schematic diagram of a battery operated flame ionization detector (FID) system in accordance with one or more implementations of various technologies described herein.

The discussion below is directed to certain specific implementations. It is to be understood that the discussion below is only for the purpose of enabling a person with ordinary skill in the art to make and use any subject matter defined now or later by the patent "claims" found in any issued patent herein.

The following paragraphs provide a brief executive summary of one or more implementations of various technologies directed to a battery operated flame ionization detector (FID). In one implementation, the battery operated FID may be used in conjunction with a Personal Digital Assistant (PDA) to monitor whether gases are leaking from gas containing devices.

In operation, the battery operated FID may be used by an operator in an industrial plant to determine whether various gas-related components (e.g., Leak Detection and Repair components) are leaking. The operator may use a probe to obtain air samples around the various components. The air samples may then be fed into the battery operated FID to determine whether any VOCs are included in the air samples. If VOCs are detected in the air samples, the operator may determine that the various components from which the air samples have been obtained are leaking.

In order to determine whether any VOCs are included in the air samples, the battery operated FID combusts the air sample using a flame inside a detector region of the battery operated FID. In one implementation, the operating conditions inside the detector regions should remain constant in order to accurately determine whether any VOCs are indeed included in the air samples. As such, the battery operated FID may be equipped with various types of sensors to provide information pertaining to various parts of the battery operated FID to a controller. The controller may be used to maintain the operating conditions inside the detector region by controlling the flow of air sample or hydrogen gas into the detector region.

Pump Throttling

In one implementation, the controller may receive information pertaining to the downstream air pressure of a tube that provides the air sample to the detector region using an air pump. If the controller determines that the downstream air pressure is too low, the controller may increase the voltage supplied to the air pump, thereby increasing the flow rate of the air traveling through the air pump and increasing the downstream air pressure. Similarly, if the controller determines that the downstream air pressure is too high, the controller may decrease the voltage supplied to the air pump, thereby decreasing the flow rate of the air traveling through the air pump and decreasing the downstream air pressure.

Ventilation

In another implementation, if the controller determines that the downstream air pressure is too low, the controller may close a needle valve that is used to provide ambient air to the tube that provides the air sample to the detector region, thereby increasing the downstream air pressure. Similarly, if the controller determines that the downstream air pressure is too high, the controller may open the needle valve that is used to provide ambient air to the tube that provides the air sample to the detector region, thereby decreasing the downstream air pressure.

Temperature

In yet another implementation, the controller may receive information pertaining to the temperature of the detector region of the FID. If the controller determines that the temperature is too low, the controller may decrease the voltage supplied to the air pump, thereby decreasing the flow rate of the air traveling through the air pump and increasing the temperature of the detector region. Similarly, if the controller determines that the temperature is too high, the controller may increase the voltage supplied to the air pump, thereby increasing the flow rate of the air traveling through the air pump and decreasing the temperature of the detector region.

Alternatively, if the controller determines that the temperature is too low, the controller may open a needle valve coupled between a hydrogen gas source and the detector region, thereby increasing the presence of hydrogen gas inside the detector region and increasing the temperature of the detector region. Similarly, if the controller determines that the temperature is too high, the controller may close a needle valve coupled between a hydrogen gas source and the detector region, thereby decreasing the presence of hydrogen gas inside the detector region and decreasing the temperature of the detector region.

Pump Power Watch

In addition to maintaining the operating conditions inside the detector region of the FID, the controller may indicate to the operator when the air pump inside the FID has reached its maximum capacity or a predetermined capacity. In one implementation, when the controller determines that the air pump has reached a predetermined capacity, the controller may display a message to the operator indicating that the air pump can no longer increase its capacity. In another implementation, the controller may turn off the voltage supply coupled to the air pump after the air pump has reached a predetermined capacity in order to prevent the controller from receiving inaccurate results from the detector region.

Pressure-Time Watch

In yet another implementation, the controller may detect the presence of water or debris in the air pump by monitoring the air pressure of the tube that provides the air sample to the detector region over time. If the air pressure changes too quickly, the controller may determine that the probe has inhaled a liquid or debris that would cause the FID to create less accurate results. In this case, when the change in the air pressure over time is above or below a predetermined value, the controller may turn off the voltage supply coupled to the air pump to prevent the controller from receiving inaccurate results from the detector region and from causing damage to the FID.

Filter Watch

In still another implementation, the controller may detect whether a filter disposed inside a probe is clogged by monitoring the air flow or vacuum pressure at a point between a sample input of the probe and the detector region. In order to monitor the air flow or the vacuum pressure, the FID may include a flow meter or a vacuum gauge disposed between a sample input of the probe and the detector region. If the air flow value or the vacuum pressure value changes too quickly, the controller may determine that the filter is clogged, which would cause the FID to create less accurate results. When the change in the air flow or vacuum pressure is above or below a predetermined value, the controller may turn off the voltage supply coupled to the air pump to prevent the controller from receiving inaccurate results from the detector region.

One or more implementations of various technologies and techniques in connection with monitoring and controlling various operating conditions inside the detector region of a battery operated FID will now be described in more detail with reference to FIGS. 1-7 in the following paragraphs.

FIG. 1 illustrates a schematic diagram of a battery operated FID system 100 in accordance with one or more implementations of various technologies described herein. The system 100 may include one or more gas sources 110, a probe 120, one or more FIDs 140 and a PDA 150.

The gas sources 110 may include may include valves, pumps, compressors, connectors, flanges, and other devices that are typically found on major equipment at industrial plants. Examples of major equipment include pumps, compressors, exchangers, tanks and vessels. In one implementation, an operator may direct probe 120 near gas sources 110 such that FID 140 may receive a sample of the air surrounding gas sources 110.

After receiving the air sample from the gas sources 110, FID 140 may route the air sample to its detector region and combust the air sample. Based on the combustion properties of the combusted air sample, FID 140 may determine whether the air sample includes volatile organic chemicals, emissions gases, nitro-aromatics, chemical warfare agents and the like. In one implementation, the FID 140 may use a battery power source such that it may be easily transported to different locations. In another implementation, FID 140 may not include a video display or any other input/output peripherals, thereby decreasing the size of FID 140. However, it should be understood that some implementations may provide options for various input/output modules and/or power sources. FID 140 and its components will be described in greater detail with reference to FIG. 2 below.

FID 140 may communicate with PDA 150 via a wired or wireless connection 130. In one implementation, PDA 150 may communicate with FIDs 140 via Bluetooth® communications. Although various implementations described herein are with reference to Bluetooth® communications, it should be understood that in some implementations, other types of communication methods may be used, such as serial cable, Ethernet cable, the Internet, and the like. PDA 150 may be used to monitor various properties of FID 140 and send commands to FID 140 such that it may control various parameters inside FID 140. Additional details with regard to PDA 150 are provided below with reference to FIG. 3.

Figure 2:
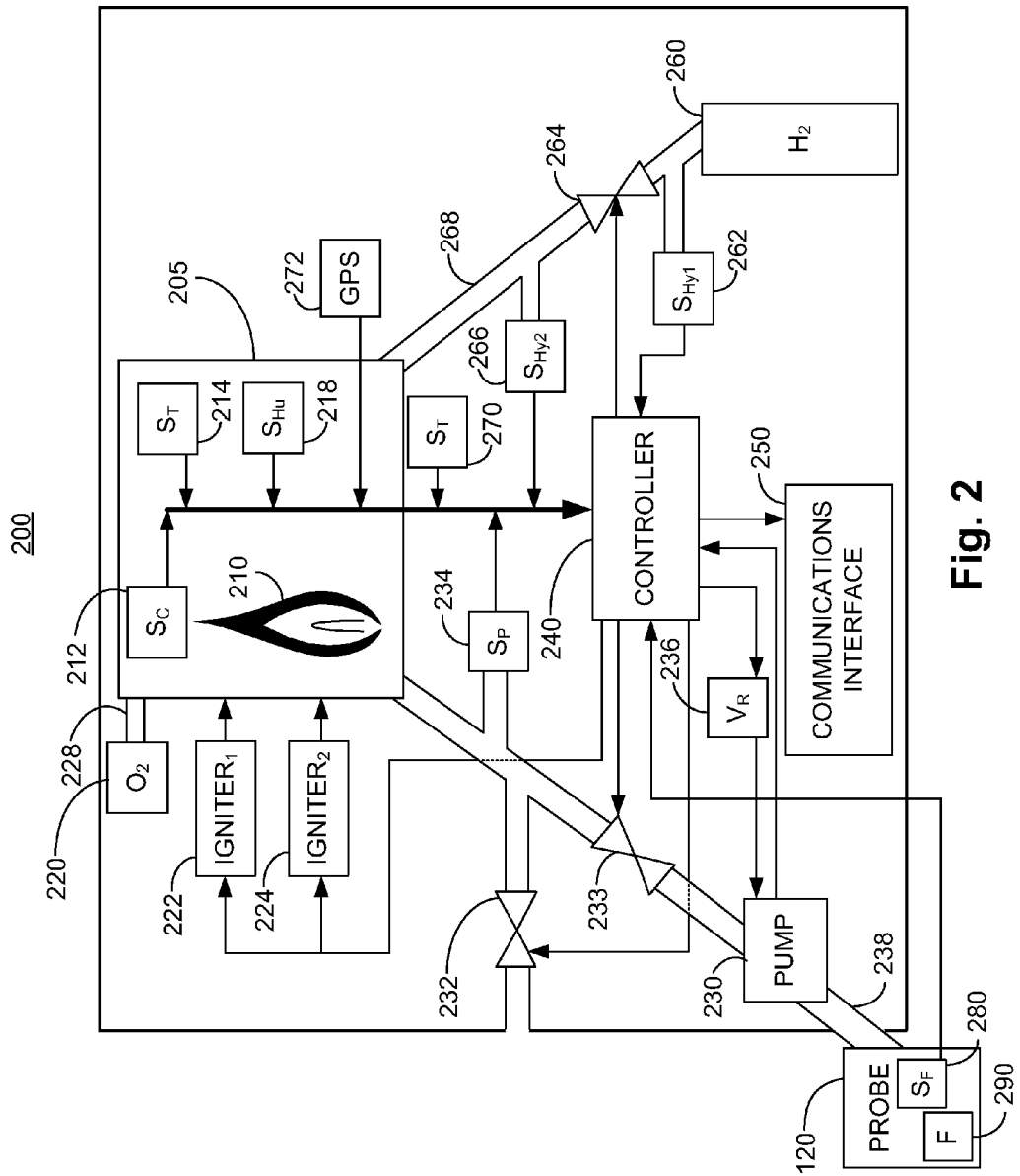
FIG. 2 illustrates a schematic diagram of a FID device in accordance with implementations of various technologies and techniques described herein.

FIG. 2 illustrates a schematic diagram of a flame ionization detector (FID) device 200 in accordance with implementations of various technologies and techniques described herein. The following description of FID 200 is made with reference to FID system 100 of FIG. 1. FID 200 may include detector region 205, oxygen supply 220, igniter 222, igniter 224, air pump 230, needle valve 232, needle valve 233, downstream air pressure sensor 234, voltage regulator 236, controller 240, communications interface 250, hydrogen supply 260, upstream hydrogen pressure sensor 262, needle valve 264, downstream hydrogen pressure sensor 266, temperature sensor 270, filter sensor 280 and filter 290.

Detector region 205 may be a separate enclosed chamber within FID 200. In one implementation, detector region 205 is insulated such that environmental conditions outside FID 200 do not affect the environment or operating conditions within detector region 205. Detector region 205 may include flame 210, combustion sensor 212, temperature sensor 214 and humidity sensor 218.

In one implementation, probe 120 may be coupled to 200 via tubing that is coupled to air pump 230. Air samples from gas sources 110 may be drawn into probe 120 and FID 200 by air pump 230. Air pump 230 may be coupled to tube 238 such that tube 238 may direct the flow of the air samples from probe 120 to detector region 205. Air pump 230 may control the rate at which the air flows through tube 238 and into detector region 205 based on the voltage it receives from voltage regulator 236. As such, voltage regulator 236 may supply air pump 230 with varying voltage amounts. In one implementation, voltage regulator 236 varies the voltage supplied to air pump 230 based on a pulse width modulation technique. Downstream air pressure sensor 234 may measure the air pressure inside tube 238 after the air sample passes air pump 230 but before the air sample enters detector region 205. In one implementation, the pressure measured at downstream air pressure sensor 234 may be controlled by the rate at which the air sample flows through tube 238. For instance, as the rate of the air sample that flows through tube 238 increases, the pressure measured at downstream air pressure sensor 234 also increases. Conversely, as the rate of the air sample that flows through tube 238 decreases, the pressure measured at downstream air pressure sensor 234 also decreases. In this manner, as air pump 230 controls the rate at which the air sample flows through tube 238, air pump 230 also controls the downstream air pressure. Although not shown, it should be noted that in some implementations an upstream air pressure sensor may be used to measure the air pressure inside tube 238 after the air sample passes probe 120 but before the air sample reaches air pump 230. In this manner, the pressure measured at the upstream air pressure sensor may be controlled by the rate at which the air sample flows through tube 238 according to the same method as described above.

Needle valve 232 may be coupled to tube 238 to supply ambient air to detector region 205. In one implementation, needle valve 232 is a needle valve configured to control the downstream air pressure in tube 238. The downstream air pressure may be controlled by controlling the amount of ambient air that is supplied into tube 238 via needle valve 232.

Needle valve 233 may also be coupled to tube 238 to control the flow of the air sample from air pump 230 to detector region 205. In one implementation, air pump 230 is configured to continuously pump air into tube 238 at a constant rate and needle valve 233 is then used to control the amount of air sample released into detector region 205, thereby controlling the downstream air pressure in tube 238. Needle valve 232 and needle valve 233 may also be used with capillary tubing, fixed orifices or other flow restriction devices inside FID 200.

In addition to the air sample being provided into detector region 205, hydrogen supply 260 and oxygen supply 220 may also be provided to detector region 205 via tube 268 and 228, respectively. In one implementation, hydrogen supply 260 and oxygen supply 220 may be pressurized tanks stored within FID 200 and filled with hydrogen gas and oxygen gas, respectively. However, it should be noted that in other implementations hydrogen supply 260 and oxygen supply 220 may provide hydrogen and oxygen to detector region 205 via gas sources that may be outside FID 200. Oxygen is provided to detector 205 to help ensure that combustion occurs within detector 205 and to ensure that flame 210 stays aflame.

The amount of hydrogen provided into detector region 205 may be regulated by needle valve 264. Needle valve 264 may be a conventional needle valve having a small port and a threaded, needle-shaped plunger that allows for a precise regulation of the flow of the hydrogen gas. Upstream hydrogen pressure sensor 262 may be coupled to tube 238 between hydrogen supply 260 and needle valve 264. As such, upstream hydrogen pressure sensor 262 may measure the pressure in tube 268 between hydrogen supply 260 and needle valve 264. Similarly, downstream hydrogen pressure sensor 266 may be coupled to tube 268 between needle valve 264 and detector region 205. As such, downstream hydrogen pressure sensor 266 may measure the pressure in tube 268 between needle valve 264 and detector region 205.

As shown in FIG. 2, tube 228, tube 238 and tube 268 are coupled to detector region 205 such that detector region 205 may receive oxygen gas, air samples and hydrogen gas from oxygen supply 220, probe 120 and hydrogen supply 260, respectively. In one implementation, the hydrogen gas provided from tube 268 may be used to create and maintain flame 210. Flame 210 may be created using igniter 222 or igniter 224. Igniter 222 and igniter 224 may create a spark that is to be combined with hydrogen gas supplied via tube 238 to create flame 210. In one implementation, if igniter 222 does not create a spark or create flame 210, then igniter 224 may be used to create flame 210. After flame 210 is created, hydrogen gas may then be supplied continuously to flame 210 to keep flame 210 aflame.

Flame 210 may be used to combust air samples received at detector region 205 via tube 238. After combusting air samples, combustion sensor 212 may detect the ions that have been burned off of the sample air. In one implementation, combustion sensor 212 measures the detected ions in pico-amps. The detected ions may be used to identify the gases that make up the air sample, thereby detecting whether VOCs are leaking from various components.

In addition to combustion sensor 212, detection region 205 may include temperature sensor 214 and humidity sensor 218. Temperature sensor 214 may include a thermocouple configured to measure the temperature of detector region 205. Similarly, humidity sensor 218 may be configured to measure the humidity of detector region 205. Temperature sensor 270 may be disposed within FID 140 but outside detector region 205 to measure the temperature of FID 140.

In one implementation, probe 120 may include a filter sensor 280 disposed inside the probe 120 after a filter 290. Filter 290 may be used to prevent debris and other unwanted material from entering the detector region 205. Filter sensor 280 may be a flow meter or a vacuum gauge coupled to probe 120 such that the readings from the flow meter or vacuum gauge may be visible to users. As such, as the filter becomes clogged, the flow meter reading may decrease or the vacuum gauge reading may decrease to indicate a decrease in air flow or an increase in vacuum pressure, respectively. Although filter sensor 280 has been described as being disposed inside probe 120, it should be noted that filter sensor 280 may be disposed anywhere between the filter it is monitoring and detector region 205.

Each sensor described above (i.e., downstream air pressure sensor 234, upstream hydrogen pressure sensor 262, downstream hydrogen pressure sensor 266, combustion sensor 212, temperature sensor 214, humidity sensor 218, temperature sensor 270 and filter sensor 280) may be coupled to controller 240. Controller 240 may log the measurements received from each sensor in its memory or other types of storage mediums. In one implementation, controller 240 and PDA 150, may use the measured values received from each sensor to maintain the operating conditions within detector region 205. Additional details as to how controller 240 and PDA 150 maintain the operating conditions inside detector region 205 are provided below with reference to FIG. 4.

FID 140 may also include a Global Positioning Device (GPS) 272 such that the location of FID 140 may be monitored. In one implementation, GPS 272 may be used to track a technician, the FID 140 or the like.

Controller 240 may also be coupled to output devices, such as voltage regulator 236, needle valve 232, needle valve 233, igniter 222, igniter 224, needle valve 264 and communications interface 250. Communications interface 250 may include a receiver, a transceiver or any other device that would enable controller 240 to communicate wirelessly with PDA 150. In one implementation, communications interface 250 may include a wireless chip to facilitate Bluetooth®, WiFi, FM, cellular and other similar communication media. As such, communications interface 250 enables the controller 240 to communicate wirelessly with the PDA 150. Although controller 240 has been described to communicate with PDA 150 using a wireless communications interface, it should be noted that controller 240 may also communicate with PDA 150 via a wired communications interface as well. Communications interface 250 may enable FID 140 to transfer data to and update software on controller 240.

Figure 3:
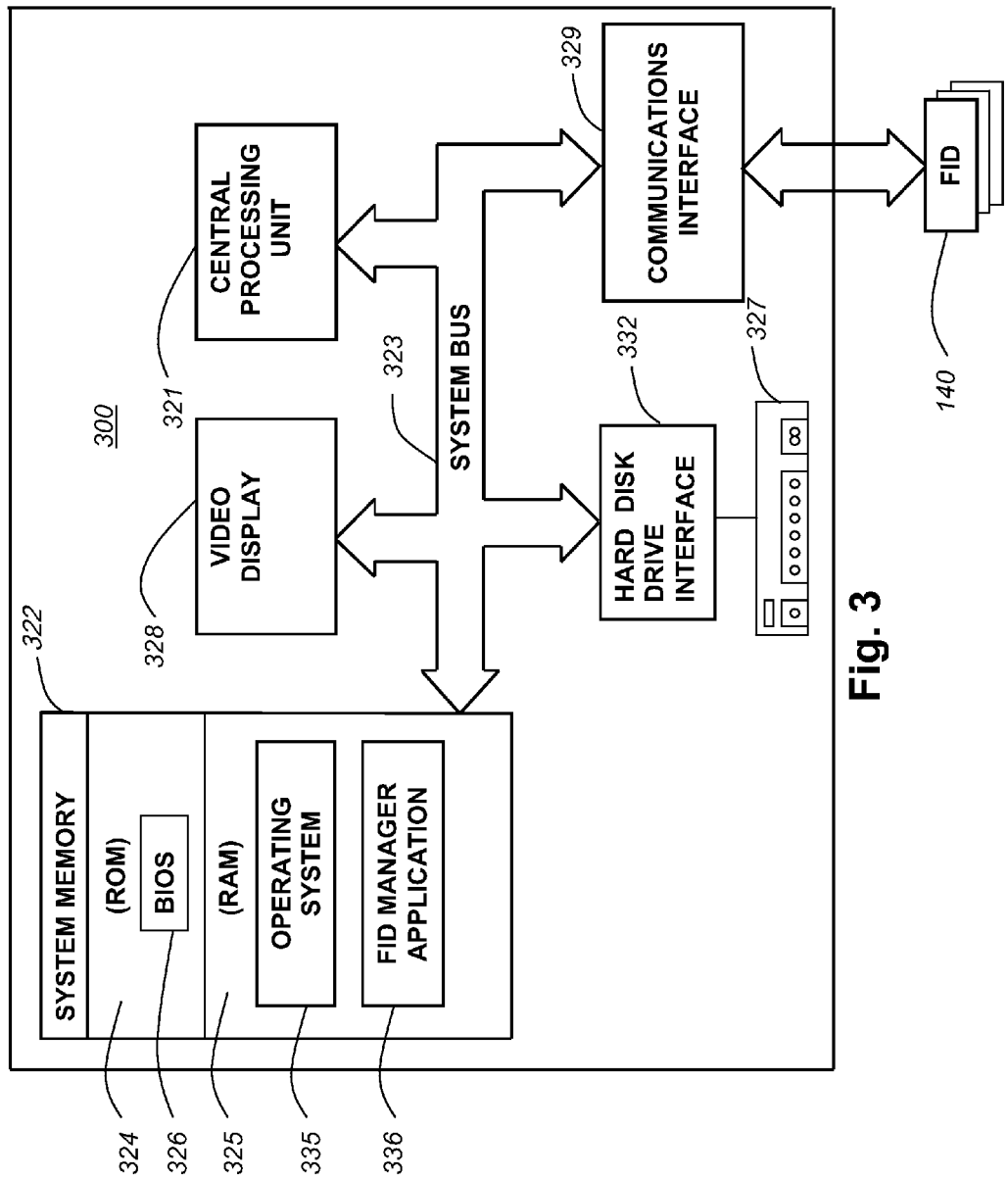
FIG. 3 illustrates a schematic diagram of a personal digital assistant (PDA) in accordance with one or more implementations of various technologies described herein.

FIG. 3 illustrates a schematic diagram of a PDA 300 in accordance with one or more implementations of various technologies described herein. PDA 300 may include a central processing unit (CPU) 321, a system memory 322 and a system bus 323 that couples various system components including the system memory 322 to the CPU 321. Although only one CPU is illustrated in FIG. 3, it should be understood that in some implementations PDA 300 may include more than one CPU. The system bus 323 may be any of several types of bus structures, including a memory bus or memory controller, a peripheral bus, and a local bus using any of a variety of bus architectures. By way of example, and not limitation, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 322 may include a read only memory (ROM) 324 and a random access memory (RAM) 325. A basic input/output system (BIOS) 326, containing the basic routines that help transfer information between elements within the PDA 300, such as during start-up, may be stored in the ROM 324. A video display 328 or other type of display device may also be connected to system bus 323 via an interface, such as a video adapter.

The PDA 300 may further include a hard disk drive 327 for reading from and writing to a hard disk. The hard disk drive 327 may be connected to the system bus 323 by a hard disk drive interface 332. The drives and their associated computer-readable media may provide nonvolatile storage of computer-readable instructions, data structures, program modules and other data for the PDA 300.

The PDA 300 may include computer-readable media that may be accessed by the CPU 321. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the CPU 321.

The PDA 300 may contain a communications interface 329 for connecting with other FIDs 140. As mentioned above, PDA 300 may interface with FIDs 140 via Bluetooth® communications. As such, the communications interface 329 may be a wireless communications interface. However, it should be understood that in some implementations the PDA 300 may use other types of communications methods.

Communication media may embody computer readable instructions, data structures, program modules or other data in a modulated data signal, such as a carrier wave or other transport mechanism and may include any information delivery media. The term "modulated data signal" may mean a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. Combinations of any of the above may also be included within the scope of computer readable media.

A number of program modules may be stored on ROM 324 or RAM 325, including an operating system 335 and FID manager 336. The operating system 335 may be any suitable operating system that may control the operation of a networked personal or server computer, such as Windows® XP, Mac OS® X, Unix-variants (e.g., Linux® and BSD®), and the like. FID manager 336 will be described in more detail with reference to FIG. 4 in the paragraphs below.

Although implementations of various technologies described herein are described with reference to the PDA 300, it should be understood that some implementations may be operational with other types of computing systems, such as laptop devices, tablet PCs, personal computers, multi-processor systems, microprocessor-based systems, programmable consumer electronics, minicomputers, and the like.

Figure 4:
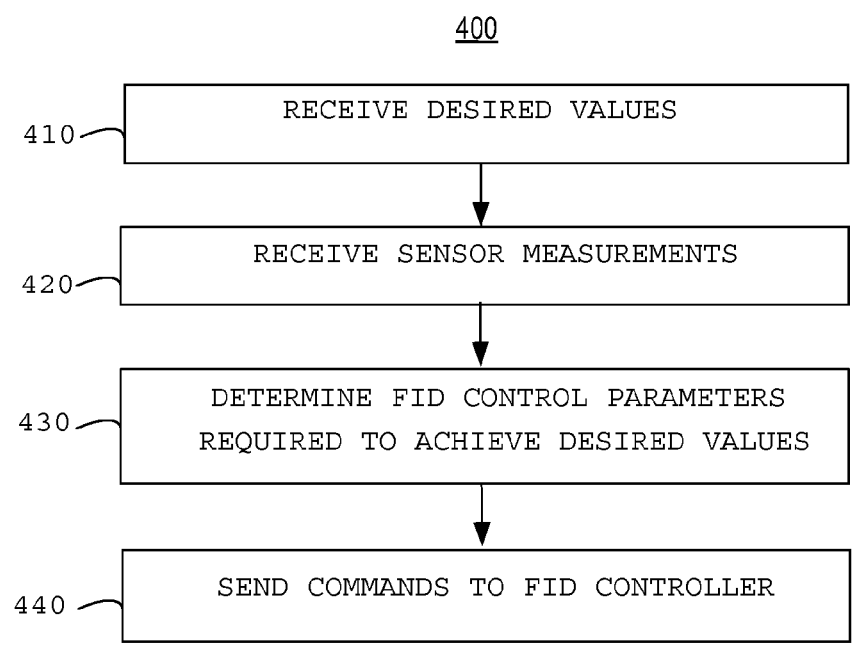
FIG. 4 illustrates a flow diagram of a method for maintaining operating conditions within a FID in accordance with implementations of various technologies and techniques described herein.

FIG. 4 illustrates a flow diagram of a method 400 for maintaining operating conditions within the detector region of a FID in accordance with implementations of various technologies and techniques described herein. The following description of method 400 is made with reference to the FIDs and PDA described in FIGS. 1-3. In one implementation, the operating conditions within detector region 205 may include the temperature, the downstream air pressure and the humidity of detector region 205. It should be understood that while the flow diagram indicates a particular order of execution of the operations, in some implementations, the operations might be executed in a different order. In one implementation, method 400 may be performed by the FID manager application 336; however, it should be noted that method 400 may also be performed by an application stored on controller 240.

At step 410, FID manager application 336 may receive desired values from an operator. The desired values may include desired measurement values for downstream air pressure sensor 234, upstream hydrogen pressure sensor 262, downstream hydrogen pressure sensor 266, temperature sensor 214 and humidity sensor 218. The desired values may describe the desired operating conditions within detector region 205. In one implementation, the desired values may include a range of measurement values that includes a low measurement threshold value and a high measurement threshold value.

At step 420, FID manager application 336 may receive measured values of downstream air pressure sensor 234, upstream hydrogen pressure sensor 262, downstream hydrogen pressure sensor 266, temperature sensor 214 and humidity sensor 218 from controller 240 via communications interface 250. The measured values may indicate the current operating conditions of detector region 205. In one implementation, FID manager application 336 may store the received measured values along with the times at which the measured values were received in its system memory 322 or hard disk drive 327.

At step 430, the FID manager application 336 may determine the control parameters that are used to achieve the desired values received at step 410. Since the desired values describe the desired operating conditions of detector region 205, the control parameters determined by FID manager application 336 may be used to control or maintain the operating conditions inside detector region 205. The control parameters may include output variables, such as the voltage output by voltage regulator 236, the opening and closing of needle valves 232, 233 or 264. For example, controller 240 may control the downstream air pressure using air pump 230 by controlling the voltage output by voltage regulator 236. Alternatively, controller 240 may control the downstream air pressure by controlling the opening and closing of needle valve 232. As another example, controller 240 may control the upstream hydrogen pressure and downstream hydrogen pressure by controlling the opening and closing of needle valve 264. The control parameters may be determined based on an algorithm that accounts for each sensor measurement received at step 420 and each output variable.

At step 440, FID manager application 336 may send commands to controller 240 to implement the control parameters determined at step 430. Various implementations for maintaining the operating conditions within detector region 205 are provided below.

Pump Throttling to Control Downstream Air Pressure

In one implementation, at step 410, FID manager application 336 may receive a desired downstream air pressure value or range of values from an operator. At step 420, FID manager application 336 may receive the downstream air pressure values that are measured by the downstream air pressure sensor 234.

If the downstream air pressure sensor 234 indicates that the downstream air pressure sensor of tube 238 is below the desired downstream air pressure value or range, FID manager application 336 may determine that the flow rate from air pump 230 should be increased in order to increase the downstream pressure value and achieve the desired downstream air pressure value. As such, FID manager application 336 may send a command to controller 240 to increase the voltage output by voltage regulator 236 to achieve the desired downstream pressure.

Alternatively, if the downstream air pressure sensor 234 indicates that the downstream air pressure sensor of tube 238 is above the desired downstream air pressure value or range, FID manager application 336 may determine that the flow rate from air pump 230 should be decreased in order to decrease the downstream pressure value and achieve the desired downstream air pressure value. As such, FID manager application 336 may send a command to controller 240 to decrease the voltage output by voltage regulator 236 to achieve the desired downstream pressure.

Ventilation to Control Downstream Air Pressure

In lieu of or in addition to throttling air pump 230 to control the downstream air pressure of tube 238, controller 240 may control the downstream air pressure of tube 238 by controlling the amount at which needle valve 232 is open. As such, if the downstream air pressure sensor 234 indicates that the downstream air pressure sensor of tube 238 is below the desired downstream air pressure value or range, FID management application 336 may determine that the ventilation provided by needle valve 232 should be moved closer to its closed position in order to increase the downstream pressure value and achieve the desired downstream air pressure value. As such, FID manager application 336 may send a command to controller 240 to close needle valve 232 in order to achieve the desired downstream air pressure value.

Alternatively, if the downstream air pressure sensor 234 indicates that the downstream air pressure sensor of tube 238 is above the desired downstream air pressure value or range, FID management application 336 may determine that the ventilation provided by needle valve 232 should be moved closer to its open position in order to decrease the downstream pressure value and achieve the desired downstream air pressure value. As such, FID manager application 336 may send a command to controller 240 to open needle valve 232 in order to achieve the desired downstream air pressure value.

In one implementation, the downstream air pressure value may decrease when foreign particles, such as dust, enter probe 120, thereby increasing the resistance in tube 238. Therefore, method 400 may be used to maintain the downstream pressure of tube 238 such that the operating conditions inside detector region 205 remains constant. By maintaining constant operating conditions inside detector region 205, FID 130 may identify VOCs in the sample air more accurately. Although the downstream air pressure has been described as being controlled using either air pump 230 or needle valve 232, it should be understood that the downstream air pressure may also be controlled using both air pump 230 and needle valve 232.

Temperature Compensator

In another implementation, at step 410, FID manager application 336 may receive a desired temperature value or range of values for detector region 205 from an operator. At step 420, FID manager application 336 may receive the temperature values measured by temperature sensor 214.

If the temperature sensor 214 indicates that the temperature inside detector region 205 is below the desired temperature value or range, FID manager application 336 may determine that the flow rate from air pump 230 should be decreased in order to increase the temperature value and achieve the desired temperature value. As such, FID manager application 336 may send a command to controller 240 to decrease the voltage output by voltage regulator 236, thereby decreasing the voltage input into air pump 230 to achieve the desired temperature.

Alternatively, the temperature values inside detector region 205 may also be controlled based on the amount of hydrogen gas being supplied into detector region 205. As such, FID manager application 336 may determine that more hydrogen should be provided into detector region 205 in order to increase the temperature inside detector region 205 and achieve the desired temperature value. As such, FID manager application 336 may send a command to controller 240 to open needle valve 264, thereby providing more hydrogen into detector region 205 until the temperature inside detector region 205 reaches the desired temperature.

Alternatively, if the temperature sensor 214 indicates that the temperature inside detector region 205 is above the desired temperature value or range, FID manager application 336 may determine that the flow rate from air pump 230 should be increased or that the hydrogen gas provided into detector region 205 supplied via needle valve 264 should be decreased in order to decrease the temperature inside detector region 205 and achieve the desired temperature value.

Temperature sensor 214 may also be used to determine whether flame 210 has ignited. After sending a command to igniter 222 to ignite flame 210, if measurements received from temperature sensor 214 are less than the predetermined temperature value, FID manager application 336 may send a command to igniter 224 to ignite flame 210. In this manner, FID 140 may use two igniters to prevent the loss of productivity due to an igniter failure. In one implementation, an operator may manually send a command to igniter 222, igniter 224 or both using FID manager application 336.

The temperature of FID 140 detected by temperature sensor 270 may also be used to determine whether various tubes within FID 140 have compressed or expanded. The compression or expansion of tubes within FID 140 may affect the rate at which air pump 230 pumps air into detector region 205. As such, method 400 may be used to alter the flow rate of air pump 230 to compensate for the compression or expansion effect to the tubes in FID 140.

Pump Power Watch

Figure 5:
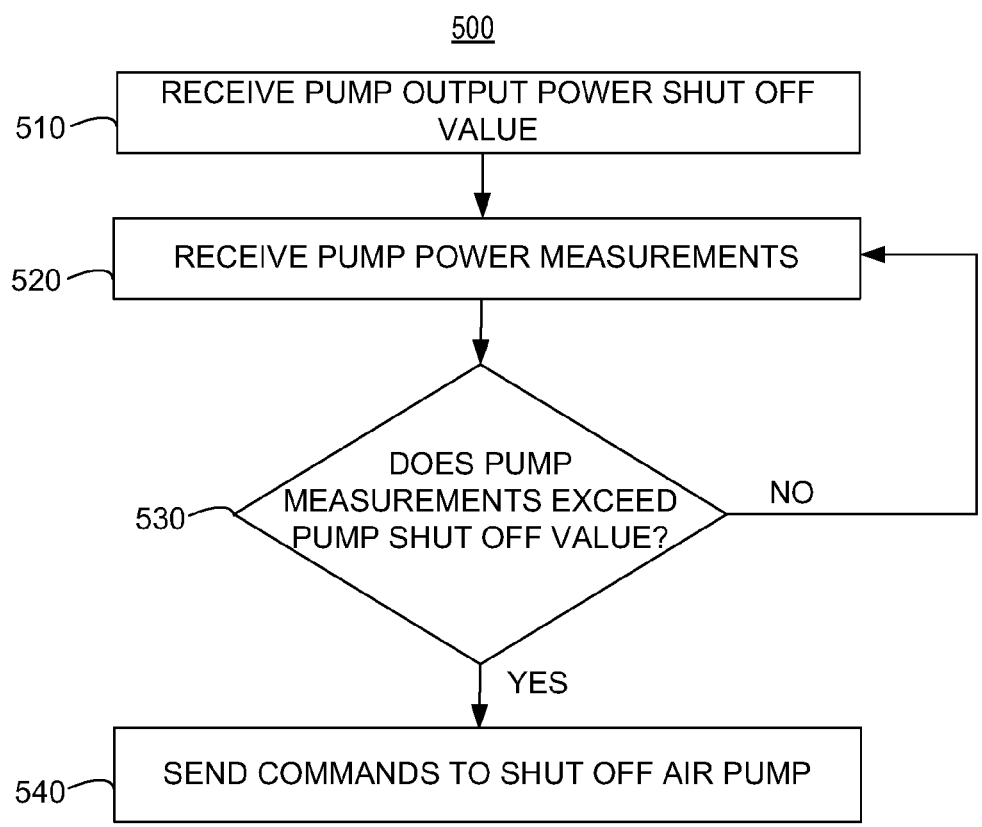
FIG. 5 illustrates a flow diagram of a method for monitoring the pump power output in a FID in accordance with implementations of various technologies and techniques described herein.

FIG. 5 illustrates a flow diagram of a method for monitoring the pump power output in accordance with implementations of various technologies and techniques described herein. The following description of method 500 is made with reference to the FIDs and PDA described in FIGS. 1-3. It should be understood that while the flow diagram indicates a particular order of execution of the operations, in some implementations, the operations might be executed in a different order. In one implementation, method 500 may be performed by the FID manager application 336, however, it should be noted that in other implementations method 500 may be performed by an application stored on controller 240.

At step 510, FID manager application 336 may receive a pump output power shut off value from an operator. The pump output power shut off value may be a value related to how much power air pump 230 may be using. The power shut off value may be based on a percentage of the maximum voltage supplied to air pump 230 from voltage regulator 236. Based on the voltage provided to air pump 230 by voltage regulator 236, FID manager application 336 may determine the percentage of power being consumed by air pump 230. In one implementation, FID manager application 336 may receive a current consumption value or a voltage level on the air pump 230.

At step 520, FID manager application 336 may determine the air pump power values based on various control parameters. For instance, FID manager application 336 may use the voltage input into air pump 230 from voltage regulator 236 and the maximum voltage available from voltage regulator 236 to determine the percentage of the power being used by air pump 230.

At step 530, FID manager application 336 may determine whether the air pump power values exceed the pump output power shut off value. If the air pump power values exceed the pump output power shut off value, FID manager application 336 may proceed to step 540. However, if the air pump power values do not exceed the pump output power shut off value, FID manager application 336 may return to step 520.

At step 540, FID manager application 336 may send commands to voltage regulator 236 to turn off the voltage supply coupled to air pump 230. By turning the voltage supply off, FID manager application 336 may effectively shut off air pump 230.

Method 500 may be used to determine whether filters in FID 140 are clogged and need to be replaced. As filters in FID 140 are clogged, air pump 230 becomes less capable of influencing the operating conditions inside detector region 205. For instance, if the air pump power values received at step 520 indicate that air pump 230 is operating at its maximum power output, air pump 230 can no longer increase its rate of flow to alter the operating conditions inside detector region 205. As such, detector region 205 may no longer be controllable and the readings from combustion sensor 212 may be inaccurate.

In one implementation, at step 540, FID manager application 336 may display a warning on its video display 328 to indicate that the air pump power values exceed the pump output power shut off value, to recommend changing the filters on FID 140, to recommend repairing or replacing air pump 230 or the like.

Pressure-Time Watch

Figure 6:
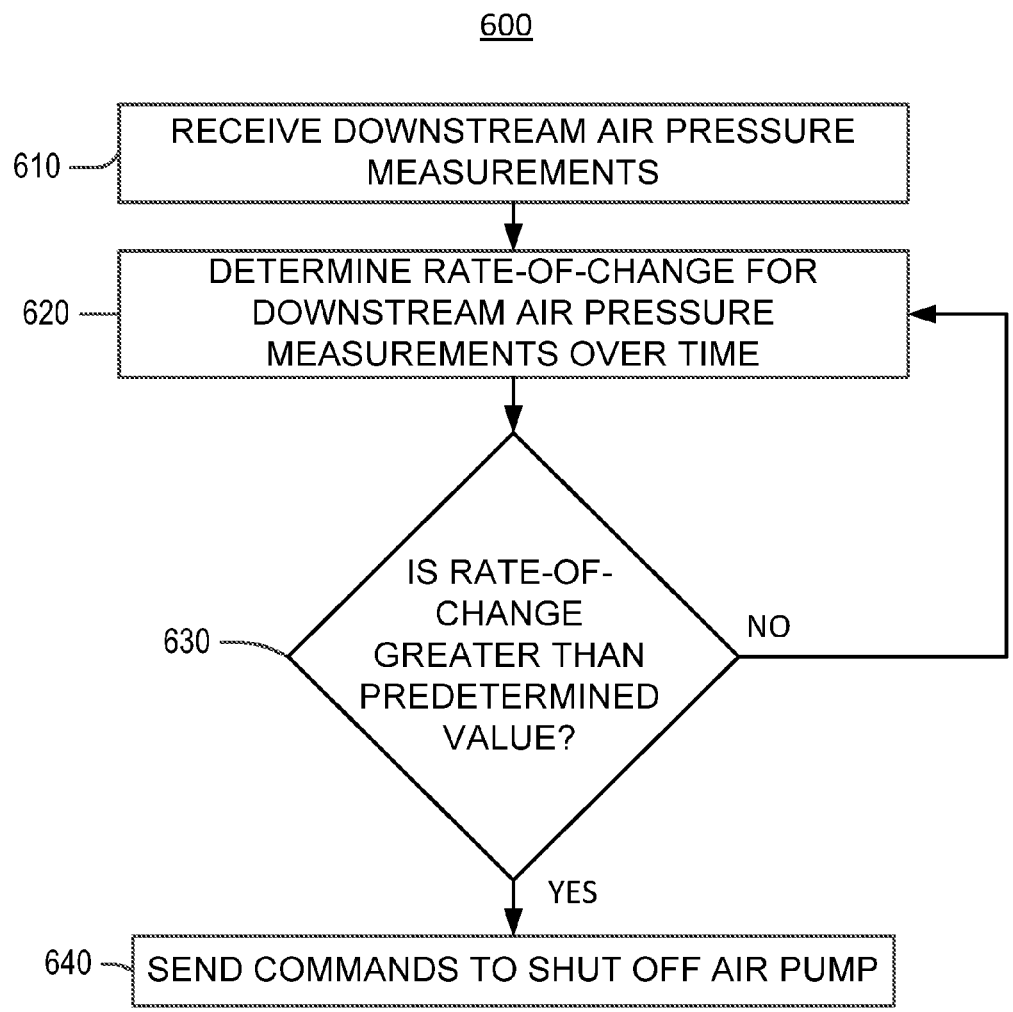
FIG. 6 illustrates a flow diagram of a method for monitoring the downstream air pressure over time in a FID in accordance with implementations of various technologies and techniques described herein.

FIG. 6 illustrates a flow diagram of a method for monitoring the downstream air pressure over time in accordance with implementations of various technologies and techniques described herein. The following description of method 600 is made with reference to the FIDs and PDA described in FIGS. 1-3. It should be understood that while the flow diagram indicates a particular order of execution of the operations, in some implementations, the operations might be executed in a different order. In one implementation, method 600 may be performed by the FID manager application 336, however, it should be noted that in other implementations method 600 may be performed by an application stored on controller 240.

At step 610, FID manager application 336 may receive measured values acquired by downstream air pressure sensor 234. In one implementation, FID manager application 336 may store the received measured values along with the times at which the measured values were received in system memory 322 or hard disk drive 327.

At step 620, FID manager application 336 may determine the downstream air pressure rate-of-change using the measured values acquired by downstream air pressure sensor 234 and their corresponding times. As such, FID manager application 336 may measure the downstream air pressure over time. In one implementation, the downstream air pressure over time measurements may be measured in terms of pounds force per square inch (PSI) per second. Although step 620 is described as determining the downstream air pressure rate-of-change using the measured values acquired by downstream air pressure sensor 234, it should be noted that in other implementations, step 620 may be performed using measured values from an upstream air pressure sensor, which may be located between air pump 230 and probe 120.

At step 630, FID manager application 336 may determine whether the downstream pressure rate-of-change is above an upper predetermined value or below a lower predetermined value. In one implementation, the predetermined value may be based on a downstream air pressure value that is observed when water or any other type of liquid or debris is inside air pump 230. For instance, when water or any debris enters tube 238, the downstream pressure over time value may increase due to the water or debris. When the downstream pressure over time value (i.e., rate-of-change value) exceeds the upper predetermined value, FID manager application 336 may proceed to step 640. However, if the downstream pressure over time value is below the upper predetermined value, FID manager application 336 may return to step 620. Alternatively, when water or any debris enters tube 238, the downstream pressure over time value may decrease due to the water or debris. When the downstream pressure over time value (i.e., rate-of-change value) decreases below the lower predetermined value, FID manager application 336 may proceed to step 640. However, if the downstream pressure over time value is above the lower predetermined value, FID manager application 336 may return to step 620.

At step 640, FID manager application 336 may send commands to voltage regulator 236 to turn off the voltage supply coupled to air pump 230. By turning the voltage supply off, FID manager application 336 may effectively shut off air pump 230.

Method 600 may be used to determine whether water or any other liquid or debris enters FID 140 via probe 120. As liquid or debris enters FID 140, detector region 205 may no longer include a controlled environment and the readings from combustion sensor 212 may be inaccurate. By monitoring the downstream pressure over time, FID manager application 336 may detect deadheading of air pump 230 and protect air pump 230 from damage caused by the deadheading. Deadheading may be caused by liquid clogging air pump 230 or liquid clogging the filters of FID 140.

Although method 600 has been described based on downstream air pressure measured values, it should be noted that method 600 may be performed based on the voltage input values provided to air pump 230 over time, the current consumption value over time or the voltage level on air pump 230 over time.

Filter Watch

Figure 7:
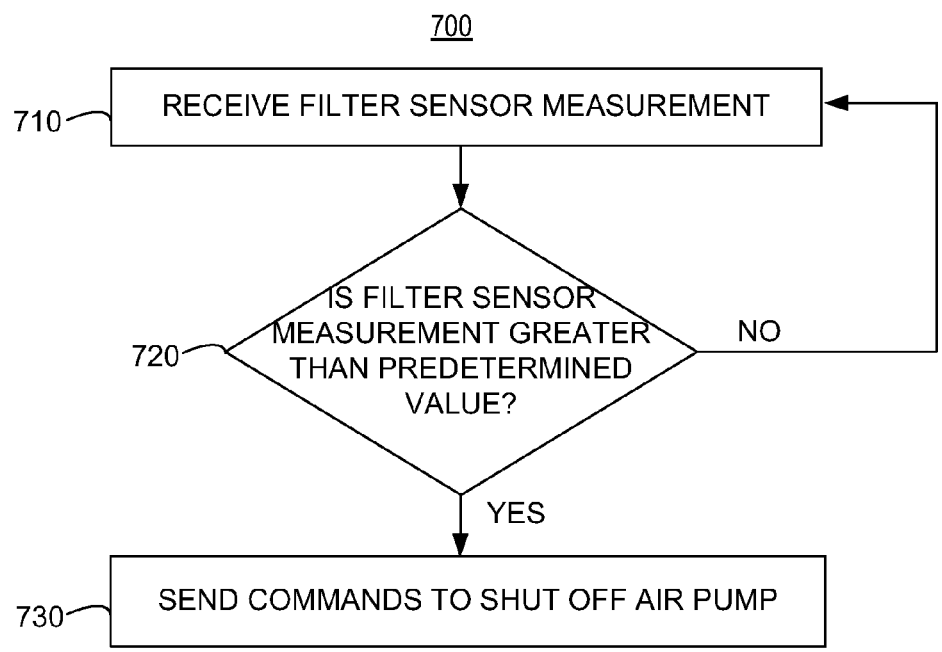
FIG. 7 illustrates a flow diagram of a method for monitoring the filter of a flame ionization detector in accordance with implementations of various technologies and techniques described herein.

FIG. 7 illustrates a flow diagram of a method for monitoring the filter 290 of a flame ionization detector 200 in accordance with implementations of various technologies and techniques described herein. The following description of method 700 is made with reference to the FIDs and PDA described in FIGS. 1-3. It should be understood that while the flow diagram indicates a particular order of execution of the operations, in some implementations, the operations might be executed in a different order. In one implementation, method 700 may be performed by the FID manager application 336, however, it should be noted that in other implementations method 700 may be performed by an application stored on controller 240.

At step 710, FID manager application 336 may receive measured values acquired by filter sensor 280. FID manager application 336 may store the received measured values in system memory 322 or hard disk drive 327. In one implementation, FID manager application 336 may receive air flow values if the filter sensor 280 is a flow meter. Alternatively, FID manager application 336 may receive vacuum air pressure values if the filter sensor 280 is a vacuum gauge.

At step 720, FID manager application 336 may determine whether the values received by filter sensor 280 are above an upper predetermined value or below a lower predetermined value. In one implementation, the predetermined value may be related to calibrated values for the filter sensor 280. The calibrated values may correspond to typical values received from filter sensor 280 after FID 140 has been calibrated. If the values received by filter sensor 280 are above the upper predetermined value or below the lower predetermined value, FID manager application 336 may proceed to step 730. However, if the values received by filter sensor 280 are not above the upper predetermined value or below the lower predetermined value, FID manager application 336 may return to step 710.

At step 730, FID manager application 336 may send commands to voltage regulator 236 to turn off the voltage supply coupled to air pump 230. By turning the voltage supply off, FID manager application 336 may effectively shut off air pump 230. In one implementation, at step 730, FID manager application 336 may display a warning message on PDA 150 to indicate that the filter 290 should be replaced.

Method 700 may be used to determine whether water or any other liquid or debris has clogged a filter system (290) that is configured to prevent debris from entering the detector region. As liquid or debris enters FID 140, detector region 205 may no longer include a controlled environment and the readings from combustion sensor 212 may be inaccurate. By monitoring the values received by filter sensor 280, FID manager application 336 may detect when a filter in the filter system should be removed and replaced.

While the foregoing is directed to implementations of various technologies described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for maintaining one or more operating conditions within a battery operated flame ionization detector (BOFID), comprising:
   receiving one or more desired values that correspond to the operating conditions;
   receiving one or more measured values from one or more sensors configured to monitor the operating conditions;
   receiving one or more time stamps, wherein the time stamps comprise the time at which at least one of the measured values was received;
   storing the measured values and the time stamps in memory or on a hard disk; and
   sending one or more commands to a controller disposed inside the BOFID to achieve the desired values based on the measured values and the time stamps.

2. The method of claim 1, wherein the desired values correspond to one or more desired temperature values inside a detector region of the BOFID.

3. The method of claim 2, wherein the sensors comprise one or more temperature sensors disposed in the detector region and wherein at least one of the measured values indicate one or more measured temperature values inside the detector region.

4. The method of claim 1, wherein sending the commands comprises:
   if the measured values are less than the desired values, then sending a first command to the controller to decrease a voltage input to an air pump disposed in the BOFID; and
   if the measured values are greater than the desired values, then sending a second command to the controller to increase the voltage input to the air pump.

5. The method of claim 4, wherein the air pump is configured to pump one or more air samples from outside the BOFID into the detector region.

6. The method of claim 4, wherein the controller increases or decreases the voltage input using a voltage regulator coupled to the air pump.

7. The method of claim 1, wherein sending the commands comprises:
   if the measured values are less than the desired values, then sending a first command to the controller to open a needle valve that is coupled between a detector region of the BOFID and a hydrogen supply; and
   if the measured values are greater than the desired values, then sending a second command to the controller to close the needle valve.

8. The method of claim 7, wherein the hydrogen supply is configured to provide hydrogen gas to the detector region for maintaining a flame inside the detector region.

9. The method of claim 1, wherein the desired values correspond to one or more desired air pressure values between an air pump and a detector region of the BOFID.

10. The method of claim 9, wherein the sensors comprise one or more pressure sensors disposed between the air pump and the detector region and wherein the measured values indicate one or more measured air pressure values between the air pump and the detector region.

11. The method of claim 1, wherein sending the commands comprises:
   if the measured values are less than the desired values, then sending a first command to the controller to increase a voltage input to an air pump; and
   if the measured values are greater than the desired values, then sending a second command to the controller to decrease the voltage input to the air pump.

12. The method of claim 1, wherein sending the commands comprises:
   if the measured values are less than the desired values, then sending a first command to the controller to close a needle valve that is coupled between ambient air and a detector region inside the BOFID; and
   if the measured values are greater than the desired values, then sending a second command to the controller to open the needle valve.

13. The method of claim 1, wherein sending the commands comprises:

if the measured values are less than the desired values, then sending a first command to the controller to open a needle valve that is coupled between the air pump and a detector region inside the BOFID; and if the measured values are greater than the desired values, then sending a second command to the controller to close the needle valve.

14. The method of claim 1, wherein the commands are sent to the controller via a wireless network.

15. The method of claim 1, further comprising:
receiving one or more temperature values measured by a temperature sensor disposed inside the BOFID but outside a detector region of the BOFID;
determining one or more compensation commands to compensate for one or more effects on one or more tubes inside the BOFID based on the temperature values, wherein the tubes are configured to transport one or more gases to the detector region; and
sending the compensation commands to the controller, wherein the compensation commands include altering a voltage input to an air pump, altering a position of a first needle valve coupled between ambient air and the detector region, altering a position of a second needle valve coupled between the detector region and a hydrogen supply, or combinations thereof.

16. The method of claim 1, further comprising:
receiving a power shut off value for an air pump disposed in the BOFID; and
if a voltage input coupled to the air pump is greater than the power shut off value, then sending a shut off command to the controller to turn the voltage input off.

17. The method of claim 1, further comprising:
receiving one or more temperature values measured by a temperature sensor disposed inside the BOFID but outside a detector region of the BOFID;
determining one or more compensation commands to compensate for one or more effects on one or more tubes inside the BOFID based on the temperature values, wherein the tubes are configured to transport one or more gases to the detector region; and
sending the compensation commands to the controller to achieve the desired values based on the temperature values.

18. The method of claim 17, wherein the compensation commands comprise altering a voltage input to an air pump coupled to a portion of the tubes located between a probe and the detector region.

19. The method of claim 17, wherein the compensation commands comprise altering a position of a needle valve coupled to a portion of the tubes located between ambient air and the detector region.

20. The method of claim 17, wherein the compensation commands comprise altering a position of a needle valve coupled to a portion of the tubes located between the detector region and a hydrogen supply.

21. The method of claim 1, further comprising:
receiving one or more measured values from one or more sensors disposed between a filter system and a detector region inside the BOFID;
comparing the measured values from the sensors disposed between the filter system and the detector region to a predetermined value; and
displaying a message indicating that a filter in the filter system should be replaced based on the comparison.

22. The method of claim 21, further comprising sending one or more commands to the controller to turn off a voltage supply coupled to an air pump disposed between the filter system and the detector region based on the comparison.

23. The method of claim 22, wherein the commands are sent when the measured values from the sensors disposed between the filter system and the detector region are above the predetermined value.

24. The method of claim 22, wherein the commands are sent when the measured values from the sensors disposed between the filter system and the detector region are below the predetermined value.

25. The method of claim 21, wherein the predetermined value is related to a calibration of the BOFID.

26. The method of claim 21, wherein the sensors disposed between the filter system and the detector region are air flow meters.

27. The method of claim 21, wherein the sensors disposed between the filter system and the detector region are vacuum gauges.

28. A method for monitoring one or more operating conditions within a battery operated flame ionization detector (BOFID), comprising:
receiving one or more air pressure values measured by one or more sensors disposed between a probe and a detector region of the BOFID;
receiving one or more time stamps, wherein the time stamps comprise the time at which at least one of the air pressure values was received by the BOFID;
determining a pressure rate-of-change value based on a change in the air pressure values and the time stamps; and
sending one or more commands to a controller disposed in the BOFID to turn off an air pump based on the pressure rate-of-change value.

29. The method of claim 28, wherein sending the commands comprises sending the commands when the pressure rate-of-change value is above a predetermined value.

30. The method of claim 28, wherein sending the commands comprises sending the commands when the pressure rate-of-change value is below a predetermined value.

31. The method of claim 28, wherein the air pump is configured to pump one or more air samples from outside the BOFID via the probe into the detector region.

32. The method of claim 28, wherein the air pressure values are upstream air pressure values measured by the sensors disposed between the probe and the air pump.

33. The method of claim 28, wherein the air pressure values are downstream air pressure values measured by the sensors disposed between the air pump and the detector region.

34. A method for monitoring one or more operating conditions within a battery operated flame ionization detector (BOFID), comprising:
receiving one or more current consumption values of an air pump disposed between a probe and a detector region of the BOFID;
receiving one or more time stamps, wherein the time stamps comprise the time at which at least one of the current consumption values was received;
determining a current consumption rate-of-change value based on a change in the current consumption values and the time stamps; and
sending one or more commands to a controller disposed in the BOFID to turn off the air pump based on the current consumption rate-of-change value.

35. The method of claim 34, further comprising:
receiving a power shut off value for the air pump disposed in the BOFID;

determining a percentage of power being used by the air pump; and sending one or more commands to the controller to turn off a voltage supply coupled to the air pump when the percentage of power is equal to or greater than the power shut off value.

36. The method of claim 35, wherein determining the percentage of power comprises:

receiving a voltage supplied to the air pump; and dividing the voltage by a maximum voltage that can be input to the air pump.

37. The method of claim 35, wherein the power shut off value is a percentage of a maximum amount of power that the air pump is capable of outputting.

38. The method of claim 35, wherein the percentage of power is determined based on the voltage being supplied to the air pump.

39. The method of claim 35, wherein the percentage of power is determined based on an amount of current being consumed by the air pump.

40. A battery operated flame ionization detector (BOFID), comprising:

a detector region having:

a temperature sensor for measuring the temperature inside the detector region; and a humidity sensor for measuring the humidity inside the detector region;

an air pump for pumping one or more air samples from outside the BOFID to the detector region;

a downstream air pressure sensor for measuring air pressure between the air pump and the detector region;

a voltage regulator for supplying a voltage to the air pump; and a controller coupled to the temperature sensor, the humidity sensor, the downstream air pressure sensor and the voltage regulator, wherein the controller is configured to store one or more time stamps in memory or a hard disk, and wherein the time stamps comprise the time at which at least one measurement from the temperature sensor, the humidity sensor or the downstream air pressure sensor was received by the controller.

41. The BOFID of claim 40, further comprising a needle valve for controlling an amount of hydrogen gas being provided from a hydrogen supply to the detection region.

42. The BOFID of claim 40, further comprising a needle valve for controlling the amount of the air samples being pumped from outside the BOFID to the detector region.

43. The BOFID of claim 40, further comprising a needle valve for providing ambient air to the detector region.

44. The BOFID of claim 40, wherein the controller is configured to send one or more values measured by the temperature sensor, the humidity sensor, the downstream air pressure sensor to a computer device via a wireless network.

45. The BOFID of claim 40, wherein the controller is configured to:

receive one or more desired values for the temperature sensor, the humidity sensor, the downstream air pressure sensor, or combinations thereof;

receive one or more measured values from the temperature sensor, the humidity sensor, the downstream air pressure sensor, or combinations thereof; and determining one or more commands for the voltage regulator to achieve the desired values based on the measured values.

46. A battery operated flame ionization detector (BOFID), comprising:

a detector region for determining a presence of a volatile organic compound (VOC) using a flame;

a temperature sensor for measuring the temperature outside the detector region;

an air pump for pumping one or more air samples from outside the BOFID to the detector region;

a downstream air pressure sensor for measuring air pressure between the air pump and the detector region;

a voltage regulator for supplying a voltage to the air pump; and a controller coupled to the temperature sensor, the downstream air pressure sensor and the voltage regulator, wherein the controller is configured to log measurements received by the temperature sensor or the downstream air pressure sensor, wherein the controller is configured to store one or more time stamps in memory or a hard disk, and wherein the time stamps comprise the time at which at least one of the measurements was received by the controller.

47. The BOFID of claim 46, further comprising:

a Global Positioning System (GPS) device inside the BOFID.

48. The BOFID of claim 46, further comprising:

a temperature sensor for determining ignition of a flame in the detector region;

a hydrogen storage tank coupled to the detector region;

a filter system configured to prevent debris from entering the detector region; and a filter sensor between the filter system and the detector region.

49. The BOFID of claim 48, wherein the filter sensor is a vacuum gauge configured to measure vacuum pressure between the filter system and the detector region.

50. The BOFID of claim 48, wherein the filter sensor is an air flow meter configured to measure air flow between the filter system and the detector region.

51. A non-transitory computer-readable medium having stored thereon computer-executable instructions which, when executed by a computer, cause the computer to:

receive one or more desired values that correspond to one or more operating conditions within a battery operated flame ionization detector (BOFID);

receive one or more measured values from one or more sensors configured to monitor the operating conditions;

receive one or more time stamps, wherein the time stamps comprise the time at which at least one of the measured values was received;

store the measured values and time stamps in memory or on a hard disk; and send one or more commands to a controller disposed inside the BOFID to achieve the desired values based on the measured values and the time stamps.

52. A computer system, comprising:

a processor; and a memory comprising program instructions executable by the processor to:

receive one or more desired values that correspond to one or more operating conditions within a battery operated flame ionization detector (BOFID);

receive one or more measured values from one or more sensors configured to monitor the operating conditions;

receive one or more time stamps, wherein the time stamps comprise the time at which at least one of the measured values was received;

store the measured values and time stamps in memory or on a hard disk; and send one or more commands to a controller disposed inside the BOFID to achieve the desired values based on the measured values and the time stamps.

53. A non-transitory computer-readable medium having stored thereon computer-executable instructions which, when executed by a computer, cause the computer to:
receive one or more air pressure values measured by one or more sensors disposed between a probe and a detector region of a battery operated flame ionization detector (BOFID);
receive one or more time stamps, wherein the time stamps comprise the time at which at least one of the air pressure values was received by the BOFID;
determine a pressure rate-of-change value based on a change in the air pressure values and the time stamps; and
send one or more commands to a controller disposed in the BOFID to turn off an air pump based on the pressure rate-of-change value.

54. A computer system, comprising:
a processor; and
a memory comprising program instructions executable by the processor to:
receive one or more current consumption values of an air pump disposed between a probe and a detector region of a battery operated flame ionization detector (BOFID);
receive one or more time stamps, wherein the time stamps comprise the time at which at least one of the current consumption values was received;
determine a current consumption rate-of-change value based on a change in the current consumption values and the time stamps; and
send one or more commands to a controller disposed in the BOFID to turn off the air pump based on the current consumption rate-of-change value.

* * * * *